United States Patent [19]

Aumueller et al.

[11] Patent Number: 5,145,966
[45] Date of Patent: Sep. 8, 1992

[54] CYCLIC AMIDES

[75] Inventors: Alexander Aumueller, Deidesheim; Hubert Trauth, Dudenhofen, both of Fed. Rep. of Germany

[73] Assignee: BASF Aktiengesellschaft, Ludwigshafen, Fed. Rep. of Germany

[21] Appl. No.: 597,876

[22] Filed: Oct. 12, 1990

[30] Foreign Application Priority Data

Oct. 13, 1989 [DE] Fed. Rep. of Germany ........ 3934176

[51] Int. Cl.$^5$ ................................. C07D 211/80
[52] U.S. Cl. ................................. 546/193; 546/194; 546/142; 546/223
[58] Field of Search ................. 546/193, 194

[56]  References Cited

U.S. PATENT DOCUMENTS

| | | | |
|---|---|---|---|
| 3,640,928 | 2/1972 | Murayama et al. | 546/217 |
| 4,548,973 | 10/1985 | Raynor | 546/193 |
| 4,743,657 | 5/1988 | Rebers | 525/281 |
| 4,778,837 | 10/1988 | Waterman | 524/89 |
| 4,838,943 | 6/1989 | Bitterli | 546/186 |
| 4,866,113 | 9/1989 | Bitterli | 546/186 |
| 4,904,779 | 2/1990 | Neumann | 544/180 |

FOREIGN PATENT DOCUMENTS

| | | |
|---|---|---|
| 241419 | 10/1987 | European Pat. Off. . |
| 3801944 | 7/1989 | Fed. Rep. of Germany . |
| 3823112 | 1/1990 | Fed. Rep. of Germany . |
| 3823536 | 3/1990 | Fed. Rep. of Germany . |

OTHER PUBLICATIONS

Herausgegeben von, Dr. R. Gachter & Dr. H. Muller, "Taschenbuch der Kunststoff-Additive", 2nd Edition, Carl Hanser Veleg, Munchen-Wein, 1983, p. 183.

*Primary Examiner*—C. Warren Ivy
*Assistant Examiner*—Celia Chang
*Attorney, Agent, or Firm*—Oblon, Spivak, McClelland, Maier & Neustadt

[57]  ABSTRACT

Cyclic amides of the general formula I

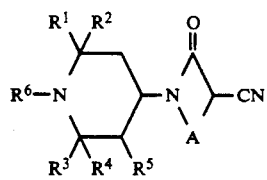

where
A is a group of the formula

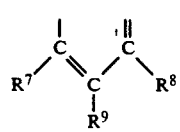 (a)

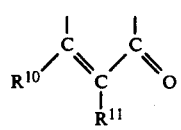

(b)

where in each case the left-hand free bond is linked to the amide nitrogen and the right-hand free bond, depending on the group, is a single or double bond, and where $R^7$ to $R^{12}$ are hydrogen, $C_1$-$C_4$-alkyl or phenyl, and $R^{13}$ is one of the radicals $R^7$ to $R^{12}$ or hydroxyl, $R^1$ to $R^4$ are $C_1$-$C_4$-alkyl, where $R^1$ and $R^2$ and/or $R^3$ and $R^4$ may in each case be linked to form a 5- or 6-membered ring, $R^5$ is hydrogen or $C_1$-$C_3$-alkyl, and $R^6$ is hydrogen, $C_1$-$C_4$-alkyl which may additionally be substituted by cyano, hydroxyl, amino or phenyl, or is $C_1$-$C_4$-acyl.

are described and are used as stabilizers for organic materials.

6 Claims, No Drawings

CYCLIC AMIDES

The present invention relates to novel cyclic amides of the general formula I

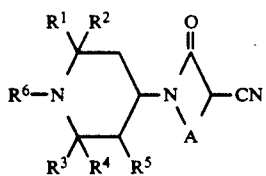

where
A is a group of the formula (a) 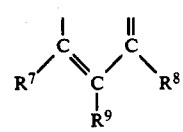

(b) 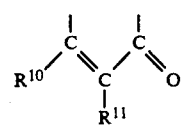

(c) 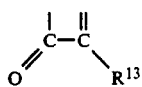

(d) 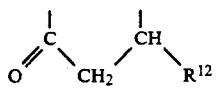

or (e) 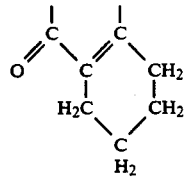

where in each case the left-hand free bond is linked to the amide nitrogen and the right-hand free bond, depending on the group, is a single or double bond, and where $R^7$ to $F^{12}$ are hydrogen, $C_1$–$C_4$-alkyl or phenyl, and $R^{13}$ is one of the radicals $R^7$ to $R^{12}$ or hydroxyl, $R^1$ to $R^4$ are $C_1$–$C_3$-alkyl, where $R^1$ and $R^2$ and/or $R^3$ and $R^4$ may in each case be linked to form a 5- or 6-membered ring, $R^5$ is hydrogen or $C_1$–$C_3$-alkyl, and $R_6$ is hydrogen, $C_1$–$C_4$-alkyl which may additionally be substituted by cyano, hydroxyl, amino or phenyl, or is $C_1$–$C_4$-acyl.

The present invention furthermore relates to a process for the preparation of these compounds, to their use as stabilizers for organic materials, and to organic materials containing these compounds which are stabilized against the action of light and heat.

It is known, for example from the earlier German Patent Applications P 38 23 112, P 38 28 536, P 38 42 304 and P 38 44 355, DE-A 38 01 944 and DE-B 19 29 928, that polyalkylpiperidine derivatives protect plastics against degradation by light and heat.

The compatibility of these piperidine derivatives with certain types of plastic, for example with polyolefins or polyamides, the duration of the protective action, the inherent color of the substances, the tendency toward volatility, and the thermal decomposition of such stabilizers at elevated temperature on incorporation into plastics are often unsatisfactory.

It is therefore an object of the present invention to provide novel stabilizers which do not have said disadvantages.

We have found that this object is achieved by the novel cyclic amides I described at the outset. $R^1$ to $R^4$ are linear or branched $C_1$–$C_4$-alkyl, such as methyl, ethyl, n-propyl, isopropyl, n-butyl or isobutyl. Furthermore, $R^1$ and $R^2$ and/or $R^3$ and $R^4$ may in each case be linked to form a 5- or 6-membered ring, preferably a cyclopentane or cyclohexane ring.

$R^5$ is hydrogen, methyl, ethyl, n-propyl or isopropyl.

$R^6$ is hydrogen, $C_1$–$C_4$-alkyl as described above, substituted $C_1$–$C_4$-alkyl, for example cyanomethyl, β-cyanoethyl, hydroxymethyl, β-hydroxyethyl, β-aminoethyl or benzyl, or $C_1$–$C_4$-acyl, such as formyl, acetyl, propionyl or butyryl.

$R^7$ to $R^{12}$ are each hydrogen, $C_1$–$C_4$-alkyl as described above, or phenyl.

$R^{13}$ is as defined for $R^7$ to $R^{12}$, or hydroxyl.

Preferred compounds I are those where

| | |
|---|---|
| $R^1$ to $R^4$ | are methyl, |
| $R^5$ and $R^6$ | are hydrogen, |
| $R^7$, $R^8$ and $R^{10}$ | are methyl, ethyl or phenyl, |
| $R^9$ and $R^{11}$ | are hydrogen or methyl, |
| $R^{12}$ | is phenyl, and |
| $R^{13}$ | is hydroxyl. |

Of the groups A, (a) and (b) are preferred.

If the cyclic amide I contains an acidic proton, the compound may also exist in tautomeric form and/or in a betaine structure.

For example, the compound Ia can exist as a tautomeric internal salt of the formula Ib

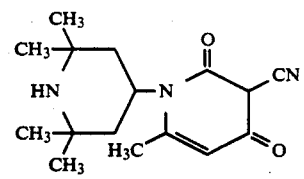

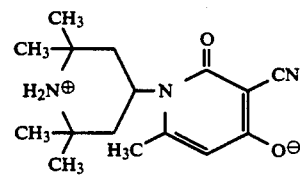

As well as in the form of the free bases and in a betaine form, the cyclic amides I can also exist as piperidinium salts containing foreign anions or as hydrates. Suitable anions originate, for example, from inorganic acids and preferably from carboxylic acids and sulfonic acids.

Examples of inorganic anions are chloride, bromide, sulfate, methanesulfonate, tetrafluoroborate, phosphate and rhodanide. Examples of suitable sulfonate anions are benzenesulfonate and tosylate. Examples of suitable carboxylate anions are formate, acetate, propionate, hexanoate, cyclohexanoate, lactate, stearate, dodecylbenzoate, benzoate, acrylate, methacrylate, citrate, malonate and succinate, and anions of polycarboxylic acids having up to about 3000 carboxyl groups.

Cyclic amides I according to the invention are expediently prepared in a conventional manner by reacting an α-cyano-N-(polyalkylpiperidyl)acetamide of the general formula II

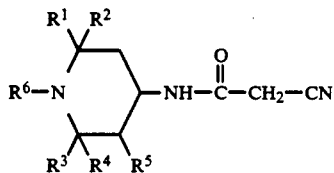

(a) with a 1,3-dicarbonyl compound, for example acetylacetone, hexane-2,4-dione, heptane-3,5-dione, benzoylacetone, dibenzoylmethane, malonaldehyde or acetylacetaldehyde, (b) with a β-carbonylcarboxylic acid ester, for example the methyl or ethyl ester of acetoacetic acid, 3-oxopentanoic acid, 2-methylacetoacetic acid, benzoylacetic acid or formylacetic acid, (c) with an oxalic acid diester, such as dimethyl or diethyl oxalate, or an α-carbonylcarboxylic acid ester, for example the methyl or ethyl ester of 2-oxopropionic acid, benzoylformic acid or glyoxylic acid, (d) with an olefinically α, β-unsaturated carboxylic acid ester, for example the methyl or ethyl ester of cinnamic acid, acrylic acid or crotonic acid, or (e) with a cyclohexanone-2-carboxylic acid ester, for example the correspondinq methyl or ethyl ester.

In general, the reaction is carried out using a basic catalyst, such as an amine, ammonia or an alkali metal hydroxide, alkoxide or carbonate. Examples of suitable amines are ethylamine, diethylamine, triethylamine, trimethylamine, morpholine and especially piperidine and pyridine. Examples of suitable basic alkali metal compounds are sodium hydroxide, potassium hydroxide, sodium carbonate, potassium carbonate, sodium ethoxide, potassium tert-butoxide and particularly sodium methoxide.

The reaction is usually carried out in a solvent, such as an alcohol, for example methanol, ethanol, n-propanol, isopropanol, n-butanol or isobutanol, an aromatic hydrocarbon or halogenated hydrocarbon, for example benzene, toluene, xylene or chlorobenzene, in an excess of the carbonyl or carboxylate compound to be reacted, normally at from 20° to 180° C., in particular from 100° to 160° C.

The cyclic amides I according to the invention are suitable for stabilizing organic materials, for example cosmetic preparations, such as ointments, pharmaceutical formulations or precursors for plastics and surface coatings, but in particular for plastics and surface coatings themselves, against the action of light and heat. They can also deactivate metal ions in the organic materials.

Examples of plastics which can be stabilized by the compounds I are polymers of monoolefins and diolefins, for example low- or high-density polyethylene, linear polybut-1-ene, polyisoprene and polybutadiene, and copolymers of monoolefins or diolefins, or mixtures of said polymers, copolymers of monoolefins or diolefins with vinyl monomers, for example ethylene-alkyl acrylate copolymers, ethylene-alkyl methacrylate copolymers, ethylene-vinyl acetate copolymers and ethyleneacrylic acid copolymers, polystyrene, copolymers of styrene or α-methylstyrene with dienes or acrylic acid derivatives, for example styrenebutadiene copolymers, styrene-acrylonitrile copolymers, styrene-ethyl methacrylate copolymers, styrene-butadiene-ethyl acrylate copolymers and styrene-acrylonitrile-methacrylate copolymers, acrylonitrile-butadiene-styrene copolymers, methyl methacrylate-butadiene-styrene copolymers and similar polymers, halogen-containing polymers, e.g. polyvinyl chloride, polyvinyl fluoride, polyvinylidene chloride, polyvinylidene fluoride and copolymers thereof, polymers derived from α,β-unsaturated acids and derivatives thereof, e.g. polyacrylates, polymethacrylates, polyacrylamides and polyacrylonitriles, polymers derived from unsaturated alcohols and amines, for example polyvinyl alcohol and polyvinylpyrrolidone, other polymers of vinyl-containing monomers, for example polyvinyl acetate, and polymers such as polyurethanes, polyamides, polyureas, polyesters, polycarbonates, polysulfones, polyether sulfones and polyether ketones.

The cyclic amides I are preferably used for stabilizing polyamides.

In addition, the compounds I can be used to stabilize surface coatings, for example industrial coatings, particularly baking enamels for the automotive industry, preferably two-coat finishes.

The cyclic amides I are mixed with the plastics and surface coatings by methods known to a person skilled in the art, the compounds I being added in a solid or, especially in the case of surface coatings, dissolved form. The good solubility of the compounds I in surface coating systems is of particular advantage here.

The present invention also provides organic materials which have been stabilized against the action of light and heat, in particular plastics and surface coatings which contain, based on the amount of organic material, from 0.01 to 5% by weight, preferably from 0.02 to 2% by weight, of one or more cyclic amides I.

In addition to the compounds I, the organic materials can also contain further auxiliaries and fillers in amounts which are customary for this purpose, for example:

further light screens, such as 2-(2'-hydroxyphenyl)-benzotriazoles, 2,4-bis(2'-hydroxyphenyl)-6-alkyl-s-triazines, 2-hydroxybenzophenones or 1,3-bis(2'-hydroxybenzoyl)benzenes, antioxidants based on phosphorus and sulfur compounds and on sterically hindered phenols, metal deactivators, such as N,N-dibenzaloxalic dihydrazide or N,N-bis[3-(3',5'-di-tert-butyl-4'-hydroxyphenyl)propionyl]hydrazine, fillers, such as carbon black, kaolin, talc or glass fibers, pigments such as titanium dioxide, and other additives, such as plasticizers, lubricants, emulsifiers, optical brighteners, flameproofing agents or antistatics.

Examples of phosphorus-containing antioxidants are tris(nonylphenyl) phosphite,
distearylpentaerythritol diphosphite,
tris(2,4-di-tert-butylphenyl) phosphite,
tris(2-tert-butyl-4-methylphenyl) phosphite,
bis(2,4-di-tert-butylphenyl)pentaerythritol diphosphite and
tetrakis(2,4-di-tert-butylphenyl)-4,4'-biphenylene diphosphite.

Examples of sulfur-containing antioxidants are
dilauryl thiodipropionate,
dimyristyl thiodipropionate,
distearyl thiodipropionate,
pentaerythritol tetrakis($\beta$-laurylthiopropionate) and
pentaerythritol tetrakis($\beta$-hexylthiopropionate).

Examples of sterically hindered phenolic antioxidants are
2,6-di-tert-butyl-4-methylphenol,
n-octadecyl $\beta$-(3,5-di-tert-butyl-4-hydroxyphenyl)-propionate,
1,1,3-tris(2-methyl-4-hydroxy-5-tert-butylphenyl)butane, 1,3,5-trimethyl-2,4,6-tris(3,5-di-tert-butyl-4-hydroxybenzyl)benzene,
1,3,5-tris(3,5-di-tert-butyl-4-hydroxybenzyl)isocyanurate,
1,3,5-tris[(3,5-di-tert-butyl-4-hydroxyphenyl)propionyloxyethyl] isocyanurate,
1,3,5-tris(2,6-dimethyl-3-hydroxy-4-tert-butylbenzyl) isocyanurate and
pentaerythritol tetrakis[$\beta$-(3,5-di-tert-butyl-4-hydroxyphenyl)propionate].

The cyclic amides I according to the invention have good compatibility with the customary types of plastic and good solubility in the customary surface coating systems. They generally have very little inherent color, if any at all, are stable and nonvolatile at the conventional processing temperatures for plastics and surface coatings, and, in particular, have a long-term protective action for the materials treated using them.

PREPARATION EXAMPLES

General method for Examples 1 to 8

0.25 mol of $\alpha$-cyano-N-(2,2,6,6-tetramethyl-4-piperidyl)acetamide, prepared from ethyl cyanoacetate and 2,2,6,6-tetramethyl-4-aminopiperidine by heating in ethanolic solution, was reacted with one of the carbonyl or carboxylate compounds listed in Table 1 in the presence of a basic catalyst, if desired in a solvent, under the reaction conditions given, and the product was then worked up.

Details of these Examples and on the products obtained are given in Table 1. Preparation conditions and yields have not been optimized.

TABLE 1

Preparation of cyclic amides I of the formula

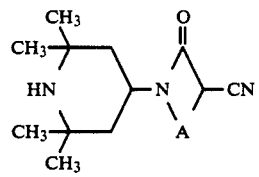

| Ex. No. | A | Carbonyl or carboxylate compound (Amount) | Solvent (Amount) | Basic catalyst (Amount) | Reaction conditions | Work-up | Yield | Color | Melting point |
|---|---|---|---|---|---|---|---|---|---|
| 1 | CH₃–C(=)–CH–C(=)–CH₃ (with CH₃ groups) | Acetylacetone (12.5 g) | Water (85 ml) | Piperidine (4 ml) | 17.5 h/100° C. | A | 10 g | colorless | 180–182° C. |
| 2 | CH₃–C–CH–C=O | Methyl acetoacetate (160 ml) | — | Piperidine (5 ml) | 1) 6.5 h/100° C. 2) 3.5 h/150° C. | B | 29 g | colorless | >320° C. |
| 3 | CH₃CH₂–C–CH–C=O | Methyl 3-oxopentanoate (100 ml) | — | Pyridine (5 ml) | 6.5 h/145° C. | C | 30 g | colorless | >310° C. |
| 4 | Ph–C–CH–C=O | Ethyl benzoylacetate (100 ml) | — | Pyridine (5 ml) | 12.5 h/160° C. | C | 6 g | colorless | >320° C. |
| 5 | CH₃–C–C(CH₃)–C=O | Methyl 2-methylacetoacetate (160 ml) | — | Pyridine (5 ml) | 1) 6 h/100° C. 2) 5 h/150° C. | D | 16 g | colorless | >320° C. |

TABLE 1-continued

Preparation of cyclic amides I of the formula

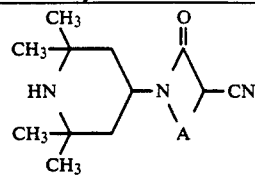

| Ex. No. | A | Carbonyl or carboxylate compound (Amount) | Solvent (Amount) | Basic catalyst (Amount) | Reaction conditions | Work-up | Yield | Color | Melting point |
|---|---|---|---|---|---|---|---|---|---|
| 6 | | Ethyl cyclo-hexanone-2-carboxylate (125 ml) | — | Pyridine (5 ml) | 17.5 h/145° C. | E | 15 g | colorless | >320° C. |
| 7 | | Methyl cinnamate (40.5 g) | Methanol (130 ml) | Sodium methoxide (1.4 g) | 48 h/25° C. | F | 14 g | colorless | 146° C. |
| 8 | | Diethyl oxalate (310 ml) | — | Pyridine (5 ml) | 14.5 h/150° C. | G | 36 g | yellowish | >320° C. |

The individual reaction batches were worked up by the following methods:

A: The mixture was cooled, and the precipitate was filtered off, washed with water and recrystallized from acetonitrile B: The mixture was cooled, the precipitate was filtered off, washed with methanol and acetone and recrystallized from acetic acid/formic acid (1.7:1), and the recrystallized product was dissolved in 15% strength sodium hydroxide solution and reprecipitated using acetic acid at pH 10–11

C: The mixture was cooled, 150 ml of ethanol were added, and the precipitate was filtered off, washed with ethanol and recrystallized from acetic acid D: The mixture was cooled, 65 ml of ethanol were added, the precipitate was filtered off and digested using 310 ml of hot dimethylformamide, and the purified product was filtered off and washed with ethanol E: The mixture was cooled, 85 ml of methanol were added, the precipitate was filtered off, washed with methanol and acetone and dissolved in a hot mixture of 85 ml of acetic acid and 125 ml of formic acid, and the product was reprecipitated by pouring the solution into water F: The precipitate was filtered off, washed with a little methanol and recrystallized from acetonitrile G: The mixture was cooled, and the precipitate was filtered off and washed with ethanol

USE EXAMPLES

STABILIZATION OF POLYAMIDE: EXAMPLES 9 TO 14

Exposure samples were produced by in each case incorporating 0.2 parts by weight of the stabilizer from Examples 1 to 5 or of a stabilizer of the prior art into 100 parts by weight of nylon 6 by one pass through an extruder at 250° C., and the granules produced were injection-molded in an injection-molding machine at 250° C. to give test specimens 2 mm in thickness.

These test specimens were tested in a Hanau Xenotest ® 1200 accelerated weathering tester for light and weathering resistance. The aging was determined by measuring the time before commencement of cracking at the surface of the test specimens.

The results are collated in Table 2 below.

TABLE 2

Stabilization of nylon 6

| Example No. | Stabilizer from Example | Time before cracking |
|---|---|---|
| According to the invention: | | |
| 9 | 1 | >2250 h |
| 10 | 2 | 2250 h |
| 11 | 3 | >2250 h |
| 12 | 4 | >2250 h |
| 13 | 5 | 2250 h |
| For comparison: | | |
| 14 | * | 1750 h |

*Compound

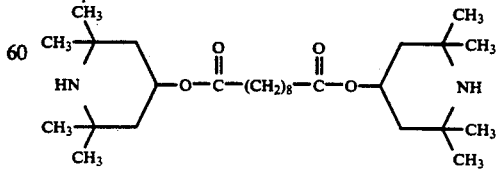

as in R. Gächter and H. Müller, Taschenbuch der Kunststoff-Additive, 2nd Edition, Carl Hanser Verlag, Munich, Vienna, 1983, p. 189

We claim:

1. A cyclic amide of the formula I

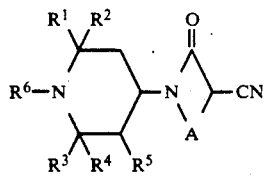

where

A is a group of the formula

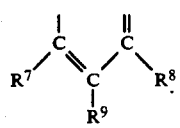

or

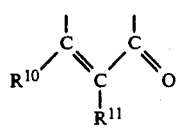

where in each case the left-hand free bond is linked to the amide nitrogen and the right-hand free bond, depending on the group, is a single or double bond, and where $R^7$ to $R^{11}$ are hydrogen, $C_1$-$C_4$-alkyl or phenyl, $R^1$ to $R^4$ are $C_1$-$C_4$-alkyl, where $R^1$ and $R^2$ and/or $R^3$ and $R^4$ may in each case be linked to form a 5- or 6-membered ring, $R^5$ is hydrogen or $C_1$-$C_3$-alkyl, and $R^6$ is hydrogen, $C_1$-$C_4$-alkyl which may additionally be substituted by cyano, hydroxyl, amino or phenyl, or is $C_1$-$C_4$-acyl.

2. A cyclic amide I as claimed in claim 1, where

| | |
|---|---|
| $R^1$ to $R^4$ | are methyl, |
| $R^5$ and $R^6$ | are hydrogen, |
| $R^7$, $R^8$ and $R^{10}$ | are methyl, ethyl or phenyl, and |
| $R^9$ and $R^{11}$ | are hydrogen or methyl |

3. A cyclic amide of the formula I

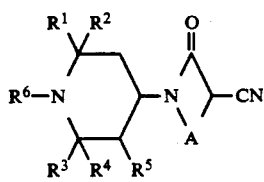

where

A is of the formula (a)

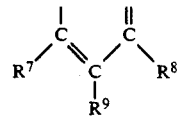

where the left-hand free bond is linked to the amide nitrogen and the right-hand free bond is a double bond, and where $R^7$ to $R^9$ are hydrogen, $C_1$-$C_4$-alkyl or phenyl, $R^1$ to $R^4$ are $C_1$-$C_4$-alkyl, where $R^1$ and $R^2$ and/or $R^3$ and $R^4$ may in each case be linked to form a 5-or 6-membered ring, $R^5$ is hydrogen or $C_1$-$C_3$-alkyl, and $R^6$ is hydrogen, $C_1$-$C_4$-alkyl which may additionally be substituted by cyano, hydroxyl, amino or phenyl, or is $C_1$-$C_4$-acyl.

4. A cyclic amide of the formula I as claimed in claim 3, where

| | |
|---|---|
| $R^1$ to $R^4$ | are methyl, |
| $R^5$ and $R^6$ | are hydrogen, |
| $R^7$ and $R^8$ | are methyl, ethyl or phenyl, and |
| $R^9$ | is hydrogen or methyl. |

5. A cyclic amide of the formula I

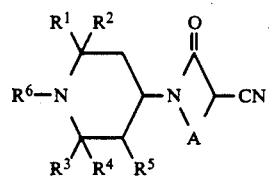

where

A is of the formula (b)

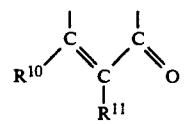

where the left-hand free bond is linked to the amide nitrogen and the right-hand free bond is single bond, and where $R^{10}$ and $R^{11}$ are hydrogen, $C_1$-$C_4$-alkyl or phenyl, $R^1$ to $R^4$ are $C_1$-$C_4$-alkyl, where $R^1$ and $R^2$ and/or $R^3$ and $R^4$ may in each case be linked to form a 5- or 6-membered ring, $R^5$ is hydrogen or $C_1$-$C_3$-alkyl, and $R^6$ is hydrogen, $C_1$-$C_3$-alkyl which may additionally be substituted by cyano, hydroxyl, amino or phenyl, or is $C_1$-$C_3$-acyl.

6. A cyclic amide of the formula I as claimed in claim 5, where

| | |
|---|---|
| $R^1$ to $R^4$ | are methyl, |
| $R^5$ and $R^6$ | are hydrogen, |
| $R^{10}$ | is methyl, ethyl or phenyl, and |
| $R^{11}$ | is hydrogen or methyl. |

* * * * *